United States Patent
Schaefer et al.

(10) Patent No.: US 6,703,038 B1
(45) Date of Patent: Mar. 9, 2004

(54) INJECTABLE BONE SUBSTITUTE MATERIAL CONTAINING NON-CERAMIC HYDROXYAPATITE CEMENT

(75) Inventors: Dirk Johannes Schaefer, Freiburg (DE); Thomas Kiefer, Freiburg (DE); Gerhard Bjorn Stark, Breitnau (DE); Ulrich Kneser, Freiburg (DE)

(73) Assignee: Universitaetsklinikum Freiburg, Freiburg (DE)

( * ) Notice: Subject to any disclaimer, the term of this patent is extended or adjusted under 35 U.S.C. 154(b) by 174 days.

(21) Appl. No.: 09/718,087

(22) Filed: Nov. 22, 2000

(30) Foreign Application Priority Data

Nov. 24, 1999 (DE) .......................................... 199 56 503

(51) Int. Cl.$^7$ ............................ A61F 2/00; C12N 11/14; C12N 11/02; C12N 5/06; C12N 5/08
(52) U.S. Cl. ..................... 424/426; 424/93.7; 435/176; 435/177; 435/395
(58) Field of Search ................ 435/174, 176, 435/177, 395; 424/422, 423, 426, 93.7

(56) References Cited

U.S. PATENT DOCUMENTS 5,914,121 A   6/1999   Robey et al. ............... 424/423

FOREIGN PATENT DOCUMENTS

| DE | 34 25 182 C2 | 1/1985 |
| DE | 42 19 321 A1 | 12/1993 |
| DE | 198 05 673 A1 | 8/1999 |
| DE | 198 12 714 A1 | 9/1999 |
| DE | 199 62 090 A1 | 6/2000 |
| WO | WO 97/14376 | 4/1997 |

OTHER PUBLICATIONS

Constantino et al., "Hydroxyapatite Cement," Archives of Otolaryngology, Apr. 1991, pp. 379–384, vol. 117, AmA.

*Primary Examiner*—David M. Naff
(74) *Attorney, Agent, or Firm*—Heller Ehrman White and McAuliffe

(57) ABSTRACT

A bone substitute material is prepared which comprises a soft matrix, living cells and a setting matrix comprising non-ceramic hydroxyapatite cement. The bone substitute material can be injected minimally invasively into a bone defect with a suitable injection apparatus. In an embodiment, living cells are mixed with a fibrinogen solution and then with a thrombin solution to form the soft matrix, and the soft matrix is mixed with an aqueous solution of non-ceramic hydroxyapatite cement to obtain the bone substitute material which remains unsolidified until after application to a body.

7 Claims, 5 Drawing Sheets

INJECTABLE BONE SUBSTITUTE MATERIAL CONTAINING NON-CERAMIC HYDROXYAPATITE CEMENT

CROSS-REFERENCE TO RELATED APPLICATIONS

The present invention claims the benefit of application no. 199.56.503.1, filed on Nov. 24, 1999, in Fed. Republic of Germany.

BACKGROUND OF THE INVENTION

1. Field of the Invention

The present invention relates to a bone substitute material comprising living cells and a setting matrix. The invention likewise relates to processes for producing such a bone substitute material and to the use of hydroxyapatite cement for producing a bone substitute material containing living cells, and the use thereof in a suitable injection apparatus.

2. Description of the Related Art

It is desirable with many bone defects to have available a bone substitute material with which these defects can be filled. Examples of such defects in the jaw region are periodontosis or atrophies, in the hand region are defects after bone tumor resections and trauma and defects of the spine, the skull and the long bones, for example associated with osteoporotic fractures and tumor resections.

Various bone substitute materials are known in the prior art. Bone substitute materials which can be molded are often referred to as "injectable bone". Solutions covered by this term to date comprise either hydrogels with bone-forming cells, hydrogels with osteoinductive proteins or polymers which solidify in situ, with or without osteoinductive factors. Each of these solutions has specific disadvantages. Either the materials contain no bone-forming cells, and thus are unable to have osteogenic effects. Ordinarily, a biomaterial or bone cement is injected into a bone defect as homogeneous filling which cannot be absorbed and replaced by bone. Mechanical stress leads to fatigue and fracture of the implant.

Although materials which comprise cells display potential osteogenicity, they have no stability. It is moreover not possible to shape these materials, usually in the form of hydrogels, and they have no plasticity. Polymers which set in situ often have toxic effects on the cells. U.S. Pat. No. 5,914,121 discloses a composition for implantation into a mammal comprising fibroblasts, hydroxyapatite powder and fibrin. This composition displays no secondary stability because the material does not solidify after implantation but continues to be deformable. The reason for this is that ceramic hydroxyapatite powder is used. This composition does not set because the particles do not bind together with one another. There is no prior art bone substitute material which comprises living cells and thus is able to have osteogenic effects and, at the same time, provides adequate secondary stability.

There is thus a pressing need for an advantageous bone substitute material.

BRIEF SUMMARY OF THE INVENTION

The object has been achieved by the bone substitute material of the invention, which comprises a soft matrix, living cells and a setting matrix. We have developed a suitable mixing and application unit for the bone substitute material of the invention which displays excellent primary and secondary stability. The primary stability (also "primary plasticity") of a bone substitute material means the stability of a composition at the time of application. The bone substitute material of the present invention is plastically moldable and can be converted into specific three-dimensional shapes depending on anatomical requirements. The material is thus not too "fluid" because it would then be impossible to shape any plastic structures. However, it is not too rigid either, even hardening completely in the extreme case, because it would then be impossible to adapt easily to the circumstances of the case, and because such "hard" implants normally could not contain any osteogenic components. Secondary stability means the stability of the implant after the intervention. The bone substitute material of the invention retains the three-dimensional shape conferred on it for a long time after setting. It is stable to pressure. This is achieved by the fact that the material of the invention, which has previously been shaped appropriately, completely sets within a relatively short time.

DETAILED DESCRIPTION OF THE INVENTION

Figure 1:
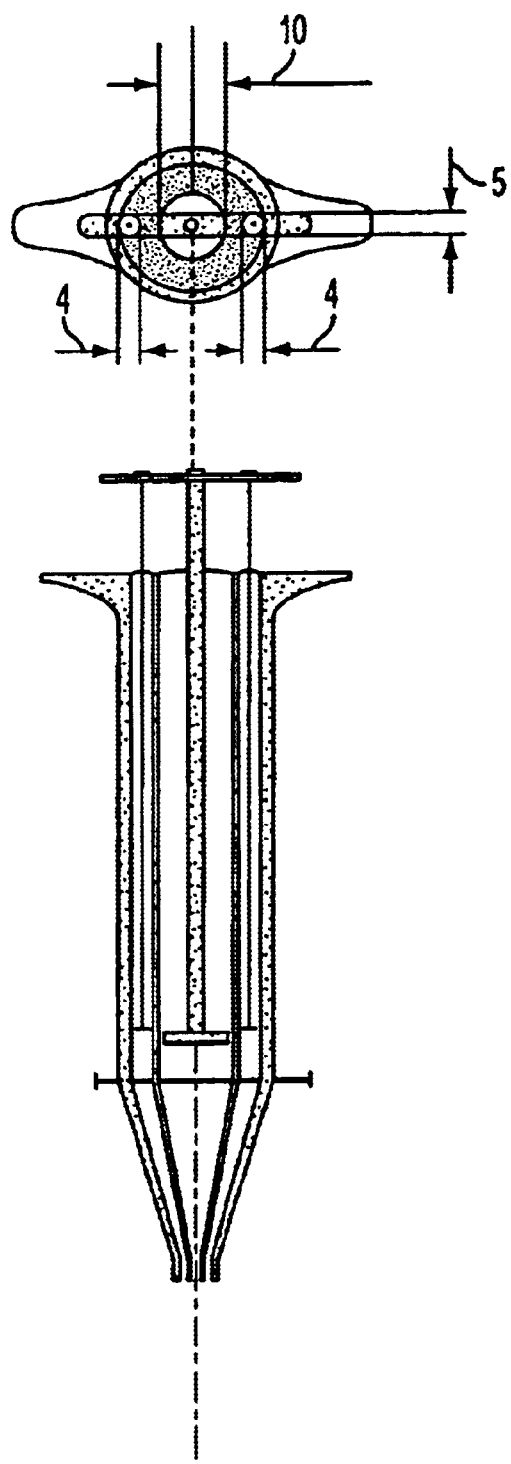
FIG. 1 shows a three-chamber syringe by which the bone substitute material of the invention can be mixed and applied.

The soft matrix ensures survival of the cells, their migration and organization in, the matrix and their differentiation to bone-forming osteoblasts. Another function of the soft matrix is that it contributes to the primary stability of the material, i.e. to the initial moldability. The soft matrix is preferably a fibrin suspension, more preferably an autogenic or allogenic fibrin suspension which can be prepared from a fibrinogen solution. This is preferably achieved by adding a thrombin-containing solution, more preferably an autogenic or allogenic thrombin-containing solution, in the presence of calcium. Before adding the thrombin it is possible to supplement the fibrinogen solution to stabilize the subsequently produced fibrin by s-amino caproic acid, aprotinin, factor 13 or similar substances. The soft matrix may, where appropriate, be supplemented with chondroitin sulfate, proteoglycans, sialoproteins, hormones or growth factors. Examples of growth factors which may be employed are bFGF, PDGF, VEGF, bone morphogenetic proteins, TGP-β and other known factors. Nucleic acids which encode the growth factors or hormones can likewise be present in the soft matrix, preferably in the form of plasmids. It is possible in addition to use other viscous, gelling and solidifying gels such as, for example, biological collagen gels, gelatin, alginates, agarose, polysaccharides, synthetic collagen, hydrogels or, viscous polymers. It is also possible to employ commercial fibrin glues such as TissuColo® (Baxter) or Beriplast (Aventis), but they are not preferred.

The living cells in the bone substitute material of the invention are preferably osteoblasts or osteoblast precursor cells. These can be obtained through small bone biopsies of the pelvis, sternum, cranium or jaw or from long bones. Alternatives to bone samples which can be used are also aspirates of bone marrow from the pelvis or from the sternum. It is possible where appropriate for the cells obtained to be cultivated and propagated in vitro. The bone substitute material also advantageously comprises angiogenic cells such as, for example endothelial cells or precursor cells thereof.

The cells are, according to the invention, either those derived from the patient himself (autologous cells) or cells or cell lines tolerated by the recipient. Examples thereof are embryonic stem cells and allogenic mesenchymal stem cells, fibroblasts, stromal cells or osteoblasts, endothelial cells, muscle cells, or precursor cells thereof are used. Autogenic mesenchymal stem cells, fibroblasts, stromal cells or osteoblasts, endothelial cells, muscle cells, or precursor cells thereof may likewise be used.

The material of the invention also comprises a setting matrix. By this means the material solidifies within a certain time to give a stable composition. The composition preferably solidifies within one hour, most preferably within 15 minutes. The bone substitute material has a pasty consistency which provides the primary stability. This means that the material can easily be adapted to a particular shape or be brought to a particular shape. The primary stability is advantageously provided by the fibrin strands present in the composition. The setting matrix is responsible for the secondary stability. This means that the composition is no longer deformable after setting but exhibits pressure resistance.

The setting matrix preferably binds together by crystallization to give hydroxyapatite. The solid matrix can be produced by inorganic compounds, for example from crystalline or amorphous calcium phosphates (tetracalcium phosphate, α or β-tricalcium phosphate, dicalcium phosphate or dicalcium phosphate dihydrate). There is preferably use of finished so called non-ceramic bone cements composed of combinations of these calcium phosphate compounds (for example BoneSource®) from Leibinger; Norian SRS® from Synthes-Stratec, USA; Biobone® from Merck, Darmstadt). These are distinguished by having an X-ray spectrometric diffraction similar to that of the mineral phase of bone, binding together endothermally or isothermally at body temperature of 37° C. in 10–15 minutes to give microporous calcium phosphate cement by crystallization, being injectable, having a pressure stability (about 60 MPA) greater than or equal to that of normal bone, entering into chemical bindings with the recipient bone, and being able to function as osteoconductive guide rail.

Calcium phosphate cement is slowly absorbed in vivo (about 35% in the first 12 months). The most preferred material for the setting matrix is non-ceramic hydroxyapatite cement. Some properties of hydroxyapatite cement are indicated in Constantino P.D. et al. (1991) Archives of Otolaryngology—Head and Neck Surgery 117, 379. Hydroxyapatite cement shows considerable differences from so-called ceramic hydroxyapatite which is frequently used in clinical practice. Hydroxyapatite cement binds together to give hydroxyapatite only by direct crystallization. The components of hydroxyapatite cement react in aqueous environment to give hydroxyapatite. Under in vitro conditions at 37°, pure hydroxyapatite cement sets in about 15 minutes. Hydroxyapatite cement for the purpose of this application is a calcium phosphate cement which binds together to give hydroxyapatite by a crystallization process.

In order to alter the injectability or the mechanical properties, it is possible to add further compounds to the calcium phosphates, such as, for example, sodium chloride solution, lactic acid, glycerol, chitosan, sodium glycerol phosphate, propylene fumarate or bioactive proteins.

It is likewise possible to employ other materials too, such as polyglycolic/lactic acid (PGLA).

The present invention thus provides an injectable bone substitute material which comprises living cells before it is administered. This distinguishes the subject matter of the invention from bone substitute materials which comprise no cells and, on the contrary, can be colonized by cells only after implantation. Materials of this type, which are usually not moldable and/or do not set, may at the most have an osteoconductive effect, i.e. as guide rail for in growth of bone tissue. In contrast thereto, the bone substitute material of the invention has an osteogenic effect, i.e. it leads to the formation of bone tissue of its own accord.

The bone substitute material of the present invention is made available in applicable form, preferably in injectable form.

A further aspect of the invention is a process for producing a bone substitute material, which comprises the following features:

a) preparation of living cells,
b) mixing of the living cells with a composition which comprises constituents to form a soft matrix,
c) mixing of the living cells with a composition which comprises a setting material.

In one embodiment of the process, the living cells are first mixed with the composition which comprises components for forming a soft matrix. After formation of the soft matrix, the living cells embedded therein are mixed with the composition which comprises a setting material. The latter mixing process preferably takes place in a special mixing chamber.

In a particular embodiment, step c) comprises the mixing and application of the living cells with a composition which comprises a setting material in one step in a mixing and application apparatus developed specifically therefor.

The cells are preferably osteoblast precursor cells which are obtained by small bone biopsies of the pelvis, sternum, cranium and jaw or from long bones. The unattached stroma is washed out of the bone samples and, after centrifugation, plated out in a culture bottle or cultivated in a bioreactor for expansion. Solid bone constituents can likewise be put in culture because further cells can be obtained therefrom by migration. This technique leads to markedly expediting the obtaining of cells and greater efficiency of yield from the same amount of material. The growing cells are usually split at the subconfluent stage and subcultured two or three times. It is also possible to use aspirates of bone marrow from the pelvis and sternum as alternatives to bone samples. The aspirates are usually rinsed into heparin medium, separated from red blood corpuscles by a density gradient centrifugation with a Ficoll or Percoll column, and plated out in a culture bottle.

A solution which comprises constituents for forming a soft matrix is preferably a fibrinogen-containing solution. The soft matrix is then produced by adding thrombin to the fibrinogen solution. Conventional fibrin glues, for example Tissucol® can also be used in principle, but these fibrin glues set to a very solid mass in which osteoblasts are no longer able to expand optimally nor migrate; this means that the osteoblasts are then able to synthesize an extracellular matrix to only a reduced extent.

It is preferred, according, to the invention for the soft matrix to be such that the cells are still able to expand and migrate, and that they also survive the presence of a setting component. In a preferred embodiment of the process of the invention, human allogenic or autogenic fibrinogen is dissolved in osteoblast culture medium, phosphate-buffered saline (PBS) or physiological saline (0.9% NaCl) and, where appropriate, stabilized with another compound, for example caproic acid or others, in order to prevent rapid enzymatic fibrinolysis by proteinases. The fibrinogen is solidified and crosslinked to give fibrin strands by addition of thrombin in a calcium chloride solution. The material produced in the calcium medium is macroscopically gelatinous and, on histological examination under a microscope, represents a three-dimensional porous network of fibrin strands. This network ensures adhesion of cells and their migration and three-dimensional organization. Reducing the thrombin concentration, and dissolving the osteoblasts in the medium lead to a slower formation of fibrin, so there is production not of a homogeneous solid clot but, on the contrary, of a three-dimensional fibrin network. Fibrinogen is preferably employed in a concentration of from 10 to 15.0 mg/ml of medium, more preferably in a concentration of from 10 to 100 mg/ml of medium, most preferably from 50 to 80 mg/ml of medium. The preferred concentration of the thrombin solution is 0.5 to 1000 I.U./ml of calcium chloride solution, a more preferred concentration is from 1 to 40 I.U./ml, and the most preferred concentration is 1 to 10 I.U./ml. It is possible to add to the fibrinogen solution as stabilizer ε-aminocaproic acid in a concentration of from 0.1 to 10% or aprotinin (500 to 5000 I.U./ml).

It is preferred for the cells after removal of the nutrient medium to be suspended in the fibrinogen solution described above. Addition of a calcium chloride-thrombin solution forms the three-dimensional fibrin network with adherent osteoblasts in the culture medium or physiological saline. It is moreover possible for there to be formation of the osteoblastic phenotype with dendritic projections on the cells, as well as intercellular links between the cells. The cells may form over the course of time an extracellular matrix around themselves, and this is subsequently mineralized. The cells maintain their normal metabolism during this and do not die.

The cell suspension is also mixed according to the invention with a composition which comprises a setting material. Preferred setting materials have been mentioned above. They are also used in the process of the invention.

The various components such as cell suspension, fibrinogen, thrombin, setting substance and others may be combined variously in solutions before the mixing. Thus, thrombin and calcium chloride can be admixed to the solution of the setting substance before the mixing process. Fibrinogen is preferably present in the cell suspension. The thrombin solution can, however, also be a separate solution. The various components can be mixed together in succession. However, they are preferably mixed together all at once. In a particularly preferred embodiment all the components are prepared under GMP conditions in a multiple syringe. An apparatus ready for injection/implantation, and a composition which is mixed during the injection process and thus initiates the setting process of fibrinogen to fibrin and of the cement powder to solid bone cement are thus made available to the user.

It is possible, for example, for calcium phosphate cement powder in a calcium chloride solution with thrombin to be drawn into one syringe of a double syringe with mouthpiece. Fibrinogen solution with suspended osteoblasts (preferably $1 \times 10^5$ to $5 \times 10^6$/ml) is drawn into the other syringe. The components are stable for about 10–15 minutes in the separated state. Injection and bringing together of the two components in a common mouthpiece leads to binding together of the fibrinogen by thrombin in the presence of calcium ions to give fibrin: The calcium phosphate cement solidifies within 15–30 minutes. It must be ensured that the components are mixed in a particular way to form microstructures such as, for example, interconnecting pores with a pore size of 100 to 800 μm.

In another preferred embodiment, a triple syringe comprising the following components is used:

1. The central syringe comprises an aqueous calcium phosphate cement solution, where appropriate with the following supplements: sodium chloride solution, lactic acid, glycerol, chitosan, sodium glycerol phosphate, propylene fumarate, bioactive proteins such as thrombin, growth factors, hormones and/or genes coding therefor in suitable vectors.
2. The lateral syringe 1 comprises a calcium chloride/thrombin solution, where appropriate with the following additions: chondroitin sulfate, proteoglycans, sialoproteins, polysaccharides and/or growth factors.
3. The lateral syringe 2 comprises a fibrinogen solution and suspended osteoblasts with, where appropriate, ε-aminocaproic acid.

It is also possible and preferable to use a complete syringe with three chambers as shown in FIG. 1. Synchronous injection results in an osteoblast/fibrin matrix being placed around a calcium phosphate cement jet with a diameter of 500–2500 μm and corresponding in three-dimensional form to cancellous bone.

It is clear to the skilled worker that the composition can also be applied in a conventional single-chamber syringe after it has previously been prepared from the various solutions or suspensions by mixing. However, separate mixing of the individual components in practical use during the operation is problematic because if there are any delays in use it is impossible to stop the mixed and thus activated components from solidifying and thus optimal flexibility is not ensured during use.

Another aspect of the invention is a device with which the injectable bone material of the present invention can be applied. The invention therefore relates to a device for preparing and administering a mixture comprising a mixing chamber with an outlet opening through which the mixture can emerge, a first supply channel (main channel) leading into the mixing chamber, and one or more other supply channels (subsidiary channels) leading into the mixing chamber, where the end of the subsidiary channel or the ends of the subsidiary channels are arranged in the mixing chamber so that material entering the mixing chamber from the subsidiary channel/subsidiary channels can penetrate into the material stream entering the mixing chamber from the main channel.

The main channel preferably has an internal diameter of more than 1 mm, more preferably of more than 1.5 mm. Viscous or highly viscous material can be introduced through this supply channel into the mixing chamber. Because of the relatively large diameter of the main channel, it is also possible for living cells embedded in a viscous matrix to be fed into the mixing chamber; only very low shear forces occur. The opening of the main channel is preferably located in the center of one wall of the mixing chamber.

The subsidiary channel/the subsidiary channels preferably have an internal diameter of not more than 1.5 mm and are normally used to feed low-viscosity materials into the mixing chamber. The most preferred internal diameter is 0.1 to 1 mm. The subsidiary channels can be, for example, hollow cannulas with an external diameter of from 0.4 to 1.5 mm. The number of subsidiary channels is at least 1, and the preferred number is 3 to 5. It is possible for the same material to be fed through each of the various subsidiary channels, but it is also possible for different materials to be fed through the individual subsidiary channels. The openings of the subsidiary channel/subsidiary channels in the mixing chamber are arranged so that material entering the mixing chamber from the subsidiary channel/subsidiary channels can penetrate into material entering the mixing chamber from the main channel. The openings of the subsidiary channels are preferably arranged symmetrically around the opening of the :rain channel in the mixing chamber, so that material emerging from them is injected into the central material stream emerging from the main channel. This injection results in very advantageous mixing of the low-viscosity components with the component of higher viscosity. This makes it possible, for example, for there to be reproducible mixing and intimate binding of the individual components directly during use. It is moreover possible to obtain mixtures with interconnecting structures with a pore size of 100–800 μm. Considerably more complex mixing devices have to date been necessary for mixing components differing greatly in viscosity.

A high-viscosity calcium phosphate mixture is preferably fed through the main channel. It is then possible in one subsidiary channel for example to feed a suspension comprising fibrinogen and living cells. In other subsidiary channels it is possible to feed additional materials, cells such as, for example, endothelial cells or other factors.

An important advantage of the device is that a mixture of the components is achieved by producing a preferred microstructure of the material which is distinguished by porosity, interconnection of the pores and a framework, preferably of hydroxyapatite, which is sufficiently stable.

Another advantage of the device of the invention is that it can be designed so that, because of a very small dead volume, only a little material remains in the device. This may be a considerable factor on application of materials which are costly or difficult to replace (cells).

In a particular embodiment, the supply lines are connected to storage containers from which the contents of the storage vessels can be delivered into the supply channels. The storage containers are preferably syringes. This has the advantage that medically standardized, sterile disposal syringes (Luer system) of varying size can be used. The syringes can be pushed into specially standardized connectors attached to the ends of the supply channels. The device may further comprise a holder for the syringes and a plunger unit with which a plurality of plungers of the various syringes can be, pushed simultaneously to empty the syringes. The syringes, the holder and the plunger unit can be designed as sterile disposable parts for medical applications.

The mixing chamber, the supply channels and the standardized connectors for the syringes are advantageously combined in one structural part, the mixing unit. It can be designed as sterile disposable part for medical applications.

The device of the invention can be used for the administration of injectable biological bone substitutes for which the creation of interconnecting microstructures minimal shear forces pressures and residual volumes the production under GMP conditions and simple handling and production of sterile, low-cost disposable structural parts are necessary. The device may, however, also be used within the framework of other concepts with similar boundary conditions. Examples are the administration of vital cells in gels or viscous systems. The advantages of the described device derive from the compatibility with conventional medical injection systems. This permits, on the one hand, the filling of disposable syringes with the various components under GMP conditions by the manufacturer and, on the other hand, the attachment of a large number of different cannulas and catheters to the outlet opening of the mixing unit, so that maximum flexibility is ensured. The invention also relates to the use of hydroxyapatite cement for producing a cell-containing bone substitute material.

The present invention provides an injectable, moldable and setting composition with a pasty consistency which contains living, preferably autogenic cells for bone formation, which are enveloped in a biological gel matrix for protection. This soft matrix component additionally ensures plastic moldability of the paste into specific three-dimensional shapes and, in vivo, the spread of synthesized bone substance and the ingrowth of blood vessels. The setting matrix ensures the dimensional stability and pressure resistance of the construct. The preferred composition of calcium phosphate stimulates osteoblasts to mature and synthesize extracellular bone matrix, for which it provides the calcium and phosphate ions. The material of the invention leads in vivo to bone formation of its own accord.

The following examples are intended to explain the invention in detail.

EXAMPLE 1

1. Establishment of an Osteoblast Culture

Various methods are available, firstly open bone biopsy (as migration or stromal cell culture) and secondly the aspiration of bone marrow, which is described below.

a) Bone Marrow Biopsy

Sterile bone biopsies are removed under local anesthesia by a hollow drill. After a small incision in the skin, 0.5 to 1 $cm^3$ blocks of spongiosa are removed, and the wound is closed. Another possibility is to aspirate about 15 ml of bone marrow.

The spongiosa should be further processed very rapidly and, if possible, be stored in a transport vessel at 4° C. for not more than 12 hours. The medium is discarded, and the spongiosa is placed in a Petri dish and reduced to small particles of 2 to 3 mm (chips) there.

aa) Migration Culture

About 3 to 4 particles are distributed in one well of a 6-well plate and covered with 3 ml of medium, or 6 to 7 chips per 25 cm² with 7 ml of medium. Incubation takes place in an incubator at 37° C. with 5% $CO_2$. The medium should be changed twice a week, with an inspection being carried out under a phase-contrast microscope. The first cells are evident after 5 to 9 days, and a subconfluent cell layer with 65 to 75% coverage of the base area is evident after 10 to 14 days.

bb) Stromal Cell Culture (own modification)

Firstly residues of muscle/connective tissue are removed from the bone. The spongiosa is reduced with scissors and, forceps to pieces of the smallest possible size. The spongiosa fragments can be placed (without medium) in a 50 ml Falcon vessel (a polypropylene screw vessel) and be weighed therewith. If the material contains a large amount of red bone marrow, a 75 cm² culture bottle can be charged later with 4 to 6 g of spongiosa. About 25 ml of medium are then added to the small pieces of spongiosa in this 50 ml Falcon vessel, and the cells are released by vortexing (high-frequency agitation process, about 30 seconds, highest stage). The supernatant is transferred into other 50 ml Falcon vessels. This step is repeated until the medium is no longer cloudy after shaking (vortexing). It is possible finally to carry out a trypsin (collagenase) treatment (about 10 minutes, 37° C.) in order to obtain more cells. The resulting c ell suspensions are centrifuged at 250 g and 4° C. for 10 minutes. Supernatants are discarded and the cell pellets are resuspended in medium and distributed in culture bottles. The washed pieces of bone can, where appropriate, be used for culturing remaining cells in a separate culture bottle (however, they should be throughly washed with medium after trypsinzation).

c) Detection of the Osteoblastic Phenotype

The osteoblastic phenotype is detected through the bone-specific proteins alkaline phosphatase and osteocalcin in the culture medium (outflow) and by immunohistochemical stains of control cultures.

EXAMPLE 2

Preparation of a Fibrin Glue 66 mg of fibrinogen are dissolved in 1 ml of culture mediumα MEM or medium 199 or BGJ-B medium) without added serum with 100 U/ml penicillin and 100 mg/ml streptomycin or physiological saline. ϵ-Amino-n-caproic acid is added in a final concentration of 0.1 to 10% of the allogenic or autogenic fibrinogen solution. 1.25 I.U. of thrombin are dissolved in 40 µl of calcium chloride solution (40 mM). Finally, 1 ml of the fibrinogen solution is mixed with 60 µl of calcium chloride/thrombin solution. The mixture is then injected into a culture dish.

EXAMPLE 3

Preparation of an Osteoblast/fibrin Suspension

Human osteoblasts and their precursor cells are obtained from a bone marrow biopsy and multiplied ex vivo as described in Example 1. The subconfluent cell culture in a 75 cm² culture bottle is tripsinized with 1 ml of 0.025% trypsin/EDTA solution for 5 minutes. The cell suspension is taken up in 2 ml of medium with 10% FCS and centrifuged at 1000 rpm and 4° C. for 5 minutes. The cell pellet is resuspended in 100 µl of medium.

After determination of the cell count, 20 000 osteoblasts (cell passage 1 to 3) are suspended in 200 µl of allogic or autogenic fibrinogen solution from Example 2. Then 60 µl of the calcium chloride/thrombin solution from Example 2 are added. The mixture is injected into a culture dish or into the wells of a 48-well plate. After addition of 760 µl of BGJ-B culture medium with 10% FCS and 100 U/ml penicillin and 100 mg/ml streptomycin, the cells are cultivated in an incubator at 37° C., 5% $CO_2$) and 100% humidity.

Under a light microscope with 100× magnification there is seen to be after 24 to 72 hours the development of the osteoblastic phenotype with dendritic cell projections, and after 5 to 12 days the construction of intercellular connections of the cells. An extracellular matrix is gradually formed around the cells and is subsequently mineralized. The vitality of the cells can be checked by trypan blue staining. To do this, the supernatant culture medium is aspirated off and then 50 µl of trypan blue solution are added. The cells are then examined under a light microscope. The trypan blue staining reveals only a few dead cells even after some weeks.

EXAMPLE 4

Preparation of a Hydroxyapatite/osteoblast Mixture

Osteoblasts are suspended in medium and added to non-ceramic hydroxyapatite which has been produced from calcium phosphate. In culture, the cells adhere to the hydroxyapatite particles. Under the electron microscope there was seen to be adhesion of the cells to the crystalline surface. The metabolism test revealed that cell metabolism was maintained by the adherent cells.

EXAMPLE 5

Production of a Hydroxyapatite Cement/fibrin Matrix

A calcium phosphate cement was added as solid constituent to the fibrin suspension. For this purpose, it was initially investigated whether the cement dissolved in water can be mixed with the fibrin/thrombin/calcium chloride complex and injected as paste. It proved possible to inject the mixture and subsequently to shape it (primary stability). It retained the shape given and solidified in minutes to a solid substance (secondary stability).

EXAMPLE 6

Production of an Osteoblast/fibrin/calcium Phosphate Cement Paste a) Fibrinogen Solution:

66 mg of fibrinogen are dissolved in 1 ml of culture medium αMEM or medium 199 or BGJ-J medium) without added serum with 100 U/ml penicillin and 100 mg/ml streptomycin or physiological saline. ϵ-Amino-n-caproic acid is added in a final concentration of 0.1 to 10% of the fibrinogen solution.

b) Fibrinogen/osteoblast Suspension:

The cell culture is established as described in Example 1. The subconfluent cell culture is trypsinized, suspended in medium and centrifuged (see Example 3). The cell pellet is resuspended in 100 µl of medium. After counting the cells, 20 000 osteoblasts (cell passage 1 to 3) are suspended in 200 µl of fibrinogen solution.

c) Calcium Phosphate/thrombin/calcium Chloridesolution:

1.25 I.U. of thrombin are dissolved in 0.5 ml of 40 mM calcium chloride solution. Then 1 g of calcium phosphate powder (BoneSource®) is added to 0.5 ml of the calcium chloride/thrombin solution.

d) Mixing of the Components:

500 µl of fibrinogen/osteoblast suspension and 500 µl of calcium phosphate/thrombin/calcium chloride solution are introduced into a 1 ml syringe. The syringe is then shaken for about 10 seconds, after which in each case about 200 µl are injected into a culture dish or 48-well plate. 800 µl of BGJ-B culture medium with 10% FCS and 100 U/ml penicillin and 100 mg/ml streptomycin are added. The cells are incubated in an incubator as described above.

e) MTS Metabolism Test (Cell Proliferation Assay):

The cell proliferation assay supplied by Boehringer Mannheim was used. It is based on the transformation of a tetrazolium salt MTS into a yellow-colored formazan by mitochondrial dehydrogenase. It takes the form of a calorimetric metabolism test. The mixtures contained 20 000 human osteoblasts (hOB) per mixture (48-well), 200 µl of fibrinogen solution (66 mg/ml) and 200 µg of calcium phosphate powder, (CaP) in 200 µl of calcium chloride/thrombin solution. After the culture medium had been aspirated off, 1 ml of MTS solution was added.

The color change in 100 µl of MTS solution in each case was determined by photometry after three hours. The various mixtures and controls are shown in the following Table I:

| Mixture | hOB 1 | hOB fibrin separate 2 | Injectable bone mixed 3 | hOB fibrin OFS mixed 4 | hOB-CaP mixed 5 | Fibrin 6 | CaP 7 |
|---|---|---|---|---|---|---|---|
| 20000 hOB | x | x | x | x | x | | |
| 200 µl fibrinogen | | x | x | x | | x | |
| 200 µg CaP | | | I x | I | I x | | I x I |

Mixtures 2 and 4 contain the same components hOB and fibrin, unmixed in mixture 2 ("separate"), and mixed as osteoblasts/fibrin suspension with OFS in mixture 4. Separate testing of the components in a mixture is intended on the one hand to make it possible to discover an adverse or beneficial effect on the cells compared with the untreated cell control (mixture 1) or absorption of the dye by the fibrin. If the cell count in mixture 2, which is checked in parallel, is the same as in mixture 1 and the absorption falls in the MTS test, then fibrin absorbs the dye: If the cell count falls on simply adding fibrin to the mixture with cells, it is to be assumed that there is a toxic effect on the hOB. In the present case, the cell count was constant, and fibrin partially absorbs the dye to be measured, but a toxic effect was precluded. This also means that the lower value for OFS (mixture 4) compared with the cell control (mixture 1) is explicable not only by the introduction of the cells into the fibrin but also by absorption. The actual metabolic activity is thus higher than indicated by the extinction.

The results of the metabolism test are shown in the following Table II:

| Mixture | Day 1 | Day 2 | Day 5 | Day 7 |
|---|---|---|---|---|
| 1 hOB | 0.31 | 0.34 | 0.4 | 0.48 |
| 2 hOB-fibrin | 0.02 | 0.18 | 0.07 | 0.15 |
| 3 Injectable bone | 0 | 0.07 | 0.14 | 0.26 |
| 4 OFS | 0 | 0.03 | 0 | 0.17 |
| 5 hOB-CaP | 0.3 | 0.15 | 0.22 | 0.18 |

-continued

| Mixture | Day 1 | Day 2 | Day 5 | Day 7 |
|---|---|---|---|---|
| 6 Fibrin | 0 | 0 | 0.003 | 0.03 |
| 7 CaP | 0 | 0 | 0 | 0 |

Figure 2:
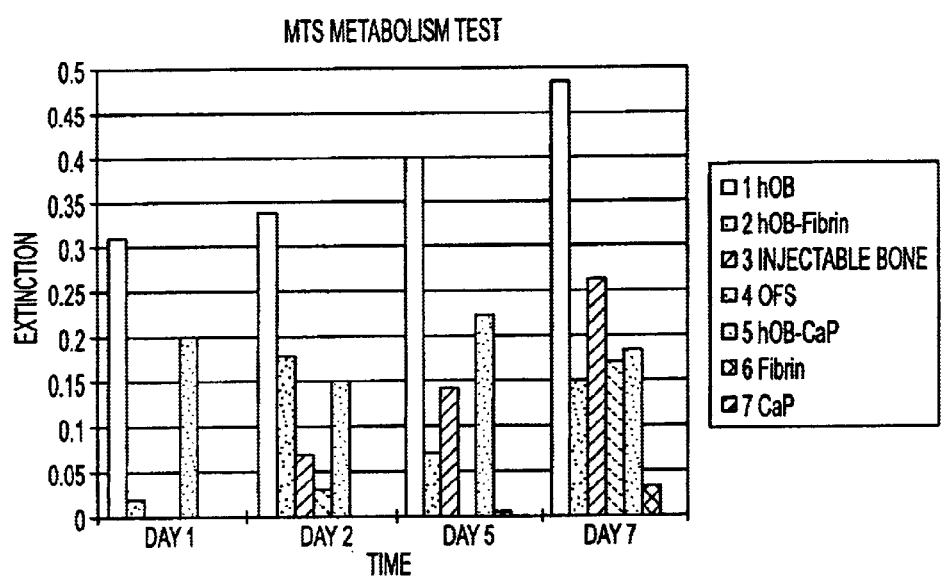
FIG. 2 shows a graphical representation of the results of an MTS metabolism test. The experiments are described in Example 6. The result demonstrates that the cells in the bone substitute material of the invention are metabolically active and survive for a considerable period.
Figure 3:
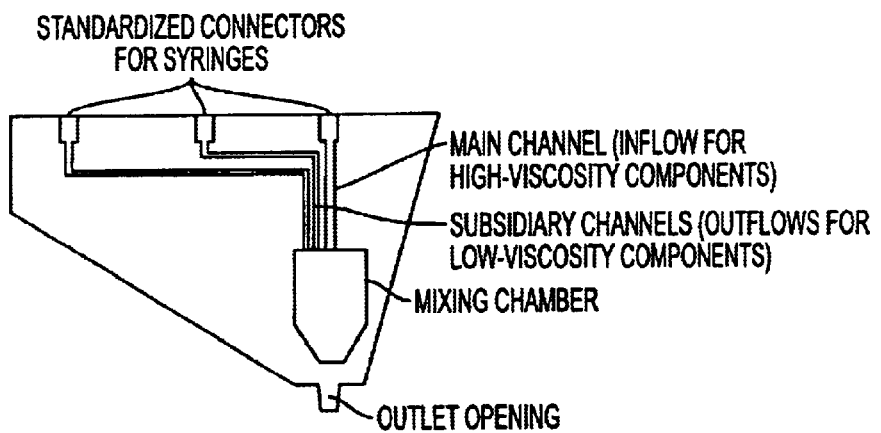
FIG. 3 shows a diagrammatic representation of a mixing unit in which the individual structural elements (main and subsidiary channels, connectors for syringes, mixing chamber with outlet opening) are combined in one structural part. It is possible to feed through the main channel for example a calcium phosphate bone cement mixture as high-viscosity component. It is possible to feed through the subsidiary channels low viscosity components, for example osteoblasts/fibrinogen suspension, additional growth and differentiation factors, plasmids and other components.
Figure 4:
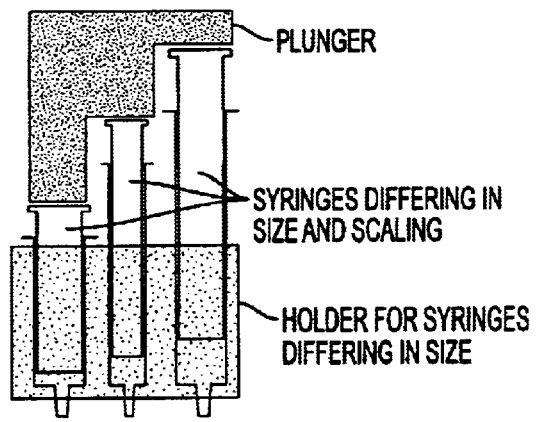
FIG. 4 shows a diagrammatic representation of a structural part comprising a plurality of syringes which are held by a holder in a particular arrangement, and a plunger with which the individual plungers of the syringes can be moved synchronously. A structural part of this type, also called applicator, can be attached to a mixing unit (FIG. 3).
Figure 5:
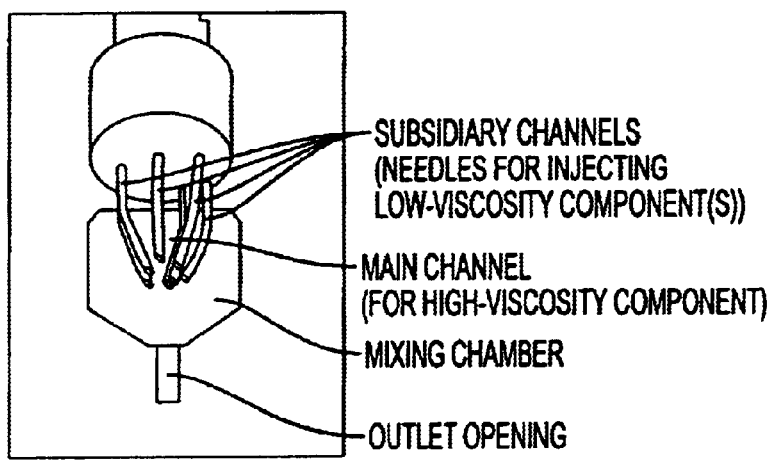
FIG. 5 shows the representation of a preferred embodiment of the device of the invention. The opening of the main channel is symmetrically surrounded by the ends, which project into the mixing chamber; of the 6 subsidiary channels which are slightly curved inward so that the material emerging from the subsidiary channels is injected into the material stream emerging from the main channel. A calcium phosphate bone cement mixture can be fed for example as high-viscosity component through the main channel. It is possible to feed through the subsidiary channels low-viscosity components, for example osteoblast/fibrinogen suspension, additional growth and differentiation factors, plasmids and other components.

FIG. 2 shows a graphical representation of the results.

EXAMPLE 7

In Vivo Test

Osteoblasts are obtained and multiplied as described in Example 1. The cells are detached enzymatically by trypsin solution. The osteoblasts ($1 \times 10^6$/ml) are suspended in a fibrinogen solution (66 mg/ml). 500 mg of BoneSource®)) calcium phosphate cement are dissolved in 0.5 ml of calcium chloride solution (40 mM) with 1.25 I.U. of thrombin/ml. 0.5 ml of fibrinogen/ osteoblast suspension is used with 0.5 ml of calcium phosphate/thrombin/calcium chloride solution to fill a 1 ml syringe and then injected subcutaneously into a nude mouse.

Nude mice about 6 to 8 weeks old were anesthetized in an anesthesia chamber with an Isofluran®)/oxygen mixture (3% Isofluran in 100% $O_2$, flow 4 1/min). While maintaining the anesthesia with an inhalation mask (1.5 to 2% by volume Isofluran in 100% $O_2$, flow 0.5 to 1 1/min), the animals were washed with Betaisodona®, and the operation field was shaved and given a sterile covering. A transverse incision about 4 mm long was made in the dorsal region. The incision was spread with dissecting scissors, and a skin pocket was created. A syringe tip was inserted and the paste was injected under the animals skin. The paste was shaped to longitudinal strands by manual percutaneous shaping. The wound was closed with interrupted sutures, and a sterile wound dressing was applied. The operation lasted about 15 minutes. The animals wounds were checked each day until wound healing was confirmed.

The nude mice finally received a lethal dose of $CO_2$ by inhalation on postoperative day 14, 29 and 48. The constructs were dissected out with the surrounding tissue, photographed and then processed histologically and immunohistochemically. The results are summarized in the following Table III:

| Mouse No. | Day | Shape | Solidity | Matrix synthesis | Vascular. |
|---|---|---|---|---|---|
| 1 | 14 | constant | pressure-stable | connective tissue | yes |
| 2 | 29 | constant | pressure-stable | incipient bone | yes. |

-continued

| Mouse No. | Day | Shape | Solidity | Matrix synthesis | Vascular. |
|---|---|---|---|---|---|
| 3 | 48 | constant | pressure-stable | bone tissue | yes |
| 4 | 29 | constant | pressure-stable | incipient bone | yes |

"Vascular." stands for vascularization, "incipient bone" stands for incipient bone formation and describes the change in—morphology from undifferentiated connective tissue to differentiated bone tissue.

The constructs were of constant size and unchanged in shape after 14, 29 and 48 days.

The histological findings were on
day 14 ingrowth of vessels and extracellular connective tissue matrix;
day 29 a network of vessels and incipient bone formation in the construct;
day 48 a network of vessels and bone tissue.

It is possible in principle to change the stated concentrations in order to achieve different characteristics in terms of cell density, solidity and moldability. Adaptation to the local conditions in a bone defect, such as exposure to pressure, shear forces, volume, is possible.

What is claimed is:

1. A process for producing a bone substitute material which comprises the following steps:
    a) preparing living cells, wherein at least some of said living cells are osteoblasts or precursor cells thereof;
    b) mixing the living cells with a fibrinogen solution and then with a thrombin solution to form a soft matrix containing said living cells; and
    c) mixing said soft matrix containing said living cells with a setting material comprising an aqueous solution of non-ceramic hydroxyapatite cement to obtain said bone substitute material,
wherein said setting material remains unsolidified before applying said bone substitute material to a body and after application to a body said setting material solidifies.

2. The process of claim 1, wherein said living cells are obtained by a bone biopsy or bone marrow aspiration.

3. The process of claim 1, wherein said living cells are cultivated in vitro before step b).

4. The process of claim 1, wherein said fibrinogens solution comprises fibrinogen dissolved in osteoblast medium or physiological saline (0.9% NaCl) or phosphate-buffered saline (PBS).

5. The process of claim 4, wherein said fibrinogen solution is stabilized by M-aminocaproic acid.

6. The process of claim 1, wherein at least one substance selected from the group consisting of chondroitin sulfate, proteoglycans, sialoproteins, growth factors, hormones and nucleic acids coding for growth factors or hormones is added to said fibrinogen solution or said thrombin solution.

7. The process of claim 1, wherein at least one substance selected from the group consisting of biological collagen gels, gelatin, alginates, agarose, polysacchardes, synthetic collagen, hydrogels and viscous polymers is added to said fibrinogen solution or said thrombin solution.

* * * * *

UNITED STATES PATENT AND TRADEMARK OFFICE
CERTIFICATE OF CORRECTION

PATENT NO. : 6,703,038 B1
DATED : March 9, 2004
INVENTOR(S) : Schaefer et al.

It is certified that error appears in the above-identified patent and that said Letters Patent is hereby corrected as shown below:

Title page,
Item [*] Notice, delete the phrase "by 174 days" and insert -- by 0 days --

Signed and Sealed this

Twenty-second Day of March, 2005

JON W. DUDAS
*Director of the United States Patent and Trademark Office*